United States Patent [19]

Chung

[11] Patent Number: 5,614,180
[45] Date of Patent: Mar. 25, 1997

[54] SHAMPOO-CONDITIONER COMPOSITION

[75] Inventor: Judy B. Chung, Glenview, Ill.

[73] Assignee: Helene Curtis, Inc., Chicago, Ill.

[21] Appl. No.: 336,825

[22] Filed: Nov. 9, 1994

Related U.S. Application Data

[63] Continuation of Ser. No. 112,950, Aug. 30, 1993, abandoned.

[51] Int. Cl.$^6$ ........................................... A61K 7/075
[52] U.S. Cl. .......................... 424/70.19; 424/70.21; 424/70.31
[58] Field of Search ..................... 424/70.19, 70.4, 424/70.31

[56] References Cited

U.S. PATENT DOCUMENTS

| | | | |
|---|---|---|---|
| 3,849,348 | 11/1974 | Hewitt | 252/547 |
| 3,855,312 | 12/1974 | Sato | 252/527 |
| 3,990,991 | 11/1976 | Gerstein | 252/542 |
| 4,374,825 | 2/1983 | Bolich, Jr. et al. | 424/70 |
| 4,392,965 | 7/1983 | Woodward et al. | 252/8.8 |
| 4,472,375 | 9/1984 | Bolich, Jr. et al. | 424/70 |
| 4,548,810 | 10/1985 | Zofchak | 424/59 |
| 4,565,647 | 1/1986 | Llenado | 252/354 |
| 4,704,272 | 11/1987 | Oh et al. | 424/70 |
| 4,844,824 | 7/1989 | Mermelstein et al. | 252/8.75 |
| 4,857,213 | 8/1989 | Caswell et al. | 252/8.75 |
| 4,902,499 | 2/1990 | Bolich, Jr. et al. | 424/70 |
| 4,913,828 | 4/1990 | Caswell et al. | 252/88 |
| 4,915,854 | 4/1990 | Mao et al. | 252/8.8 |

FOREIGN PATENT DOCUMENTS

| | | |
|---|---|---|
| 0166232 | 1/1986 | European Pat. Off. . |
| 0252551 | 1/1988 | European Pat. Off. . |
| 0294893 | 12/1988 | European Pat. Off. . |

OTHER PUBLICATIONS

Plantaren® product brochure and technical data sheets Henkel Corporation, Feb. 1992.

*Primary Examiner*—Jyothsna Venkat
*Attorney, Agent, or Firm*—Marshall, O'Toole, Gerstein, Murray & Borun

[57] ABSTRACT

A method of treating hair and a hair shampoo-conditioner composition comprising a cleansing surfactant, a water-insoluble primary amine, a sufficient amount of a suitable-acid and a carrier comprising water, are disclosed. The shampoo-conditioner compositions effectively clean and condition the hair.

27 Claims, 6 Drawing Sheets

SHAMPOO-CONDITIONER COMPOSITION

CROSS-REFERENCE TO RELATED APPLICATION

This application is a continuation of U.S. patent application Ser. No. 08/112,950, filed on Aug. 30, 1993 now abandoned.

FIELD OF THE INVENTION

The present invention is directed to a shampoo-conditioner composition and to a method of treating hair, wherein the aqueous shampoo-conditioner composition includes a water-insoluble primary amine. More particularly, a shampoo-conditioner composition of the present invention comprises: (a) a cleansing surfactant selected from the group consisting of a nonionic surfactant, an amphoteric surfactant and combinations thereof, like an alkyl polyglycoside or coco amphodiacetate; (b) a water-insoluble primary amine having about fourteen to about twenty-two carbon atoms; (c) a sufficient amount of a suitable acid selected from the group consisting of an inorganic mineral acid, an aliphatic carboxylic acid including up to about 5 carbon atoms and combinations thereof; and (d) a carrier comprising water, wherein the composition includes a sufficient amount of acid such that at least 30 mole percent of the primary amine is neutralized and such that the composition has a pH of about 4 to about 8. The shampoo-conditioner compositions optionally include a quaternary ammonium compound having one long carbon chain having about 12 to about 18 carbon atoms, a water-soluble amine at pH 6 or a mixture thereof. The shampoo-conditioner compositions simultaneously clean and condition the hair.

BACKGROUND OF THE INVENTION

Most individuals buy and use a hair shampoo for its cleansing properties. A consumer often also desires a hair shampoo that conditions the hair. However, hair shampoos generally are formulated with highly-effective anionic surfactants that are nonsubstantive to the hair and primarily cleanse the hair. Therefore, shampoos typically neither aid in the detangling of wet hair nor condition dry hair, such as improving the manageability or styleability of hair sets.

After shampooing with an anionic surfactant-based hair shampoo, the hair normally is left in a cosmetically-unsatisfactory state because anionic surfactants not only remove the dirt and soil from the hair, but also remove essentially all of the sebum naturally present on the surface of the hair fibers. Therefore, although anionic surfactants effectively cleanse the hair, hair shampoo compositions containing anionic surfactants leave the hair with an harsh, dull and dry touch, or feel, usually called "creak", after the hair is shampooed and then rinsed with water.

Thoroughly cleansed hair is extremely difficult to comb, in either the wet or dry state, because individual hair fibers tend to snarl, kink and interlock with each other. In addition, incompletely dried hair, such as hair dried with towel, has poor brushing properties, and after complete drying, the hair does not set well. Furthermore, the combing or brushing property of the hair remains poor, and the hair has undesirable electrostatic properties in a low humidity atmosphere that causes the hair to "fly away", thereby further reducing the brushing properties of the hair. The unsatisfactory combing or brushing property of hair immediately after shampooing also causes hair damage, such as split ends or hair breakage. In addition, the natural luster and resiliency of the hair is reduced. Consequently, the overall unsatisfactory condition of shampooed hair usually necessitates a subsequent post-shampoo hair treatment with a conditioning composition to improve these undesirable physical characteristics. Conditioning compositions are designed to maximize the conditioning properties of the hair and normally are applied separately from the hair shampoo. Typically, conditioning compositions are rinses or cream-like lotions containing a cationic compound that is substantive to the hair or a silicone compound.

Therefore, consumer needs traditionally have been met by the application of a shampoo to clean the hair, followed by the application of a conditioner composition to improve wet combing and other properties. The commonly-accepted method has been to shampoo the hair, followed by rinsing the hair, and then separately applying a conditioner composition, followed by a second rinse.

While numerous shampoos that include hair conditioners have been disclosed, such combination shampoos have not been totally satisfactory for a variety of reasons. In regard to shampoo-conditioner compositions, one problem relates to compatibility problems between anionic surfactants and cationic conditioning agents. This compatibility problem has caused workers in the field to investigate other surfactants, such as nonionics, amphoterics and zwitterionics, as a total or partial replacement for the anionic surfactant in shampoos. These investigations are reflected in patents issued in the shampoo conditioner area, for example, Hewitt U.S. Pat. No. 3,849,348; Gerstein U.S. Pat. No. 3,990,991; and Sato U.S. Pat. No. 3,822,312.

Accordingly, to avoid the cationic-anionic incompatibility problem, to increase the degree of conditioning imparted to the hair and to maintain the cleaning efficiency of the hair shampoo, investigators incorporated silicone compounds into anionic surfactant-based shampoo compositions. A problem inherent in formulating a silicone-based shampoo conditioner is the phase separation and foam height depression that result when a water-insoluble silicone conditioning agent is included in an aqueous shampoo-conditioner composition. A shampoo-conditioner composition of the present invention does not require a silicone conditioning agent, thereby overcoming the phase separation and foam height problems. Surprisingly, however, a shampoo-conditioner composition of the present invention conditions the hair as well as conditioner compositions including a highly-effective silicone conditioning agent.

A particularly difficult problem encountered in formulating silicone-containing shampoo-conditioner compositions is maintaining the insoluble silicone material homogeneously suspended in the composition. A variety of materials have been proposed for use in silicone-containing conditioning shampoos for the purposes of thickening and stabilization. These materials include xanthan gum, long chain acyl derivatives, long chain amine oxides, and long chain alkanolamides.

In particular, Oh et al. U.S. Pat. No. 4,704,272 discloses shampoo compositions including an anionic surfactant, a nonvolatile silicone, a hair conditioning agent and a suspending agent. The hair conditioning agent can be a tri-long chain ($C_8$–$C_{22}$) amine, such as tri(isodecyl)amine or tri-$C_{13}$ amine. Oh et al. also teach that a suspending agent, like a xanthan gum or a long chain acyl derivative, is essential to the composition. Surprisingly, it has been found that a primary amine having a carbon chain having at least 14 carbon atoms, and sufficiently neutralized with a suitable acid, provides a stable shampoo-conditioner composition that effectively cleans and conditions the hair without the need for a silicone conditioning agent or an anionic surfactant.

Bolich et al. U.S. Pat. No. 4,472,375 discloses an aqueous hair conditioning composition comprising a volatile hydrocarbon or a volatile silicone; a nonionic thickening agent; and a quaternary ammonium salt and/or a salt of a fatty amine. The composition of Bolich et al. does not include a cleansing surfactant and relies upon the nonionic thickening agent, e.g., a polymer, to suspend the water-insoluble ingredients. The present composition cleans and conditions the hair and does not require a thickener to suspend the conditioning agent. Bolich, Jr. et al. U.S. Pat. No. 4,902,499 discloses silicone polymer-containing compositions, wherein a surfactant or a fatty amine salt can be included as an optional ingredient. Bolich U.S. Pat. No. 4,374,825 discloses a hair conditioner including a volatile conditioning agent (i.e., a silicone or hydrocarbon), a nonionic water-soluble polymer and a quaternary ammonium compound or salt of a fatty amine.

Zofchak U.S. Pat. No. 4,548,810 discloses tertiary amine salts of fatty acids, wherein the fatty acid has an alkyl group of about eight to about 22 carbon atoms. The tertiary amine salts are used in cosmetic, toiletry and cleaning products, such as anionic surfactant-based shampoo products. European Patent Publication No. 0 252 551 discloses a phosphate ester or carboxylate salt of a tertiary amine used in a fabric softening or a detergent composition.

Several patents, including Caswell et al. U.S. Pat. No. 4,913,828 and European Patent Publication 0 294 893, disclose composites including a wax and an ion-pair comprising an alkyl amine or an imidazoline and an anionic surfactant, wherein the amine is a secondary or a tertiary amine. The ion pair is a chemically distinct species from either the amine or the anionic surfactant. Other patents disclosing an amine-anionic surfactant ion pair include Caswell et al. U.S. Pat. No. 4,857,213; Mermelstein et al. U.S. Pat. No. 4,844,824; and Mao et al. U.S. Pat. No. 4,915,854. Woodward et al. U.S. Pat. No. 4,392,965 discloses a laundry softener comprising a water-insoluble ion-pair compound comprising a carboxylate anion having at least ten carbon atoms and a quaternary ammonium compound having at least two carbon chains with at least twelve carbon atoms each.

A need still exists, however, for improved compositions that condition the hair, i.e., render the hair more manageable, and simultaneously clean the hair. Consequently, the present invention is directed to shampoo-conditioner compositions including a cleansing surfactant and a water-insoluble primary amine, wherein the shampoo-conditioner composition does not exhibit cationic-anionic incompatibilities, does not include additional water-insoluble conditioning agents (such as a silicone), but conditions the hair as well as present-day conditioning compositions. A present shampoo-conditioner composition effectively resists phase separation because of the presence of a sufficient amount of a suitable acid.

As will be demonstrated more fully hereinafter, a shampoo-conditioner composition, comprising: (a) a cleansing surfactant selected from the group consisting of a nonionic surfactant, an amphoteric surfactant and combinations thereof; (b) a water-insoluble primary amine having about fourteen to about twenty-two carbon atoms; and (c) a sufficient amount of a suitable acid; in (d) a carrier comprising water, effectively cleans the hair and, surprisingly, conditions the hair as well as compositions specifically designed to condition previously-shampooed hair.

SUMMARY OF THE INVENTION

In brief, the present invention relates to a composition and method of simultaneously shampooing and conditioning hair. More particularly, the present invention relates to a method of shampooing and conditioning hair by contacting the hair with a composition comprising: (a) a cleansing surfactant; (b) a water-insoluble primary amine having about 14 to about 22 carbon atoms; (c) a sufficient amount of a suitable acid selected from the group consisting of an inorganic mineral acid, an aliphatic carboxylic acid including up to about 5 carbon atoms, and combinations thereof; and (d) a carrier comprising water, wherein the composition includes a sufficient amount of acid such that at least 30 mole percent (i.e., 30 mole percent or more) of the primary amine is neutralized and such that the composition has a pH of about 4 to about 8. An aqueous hair shampoo composition of the present invention optionally includes a quaternary ammonium compound having one long carbon chain having about 12 to about 18 carbon atoms, a water-soluble amine at pH 6 or a mixture thereof. The shampoo-conditioner compositions are stable, exhibit excellent foaming and cleaning properties, demonstrate extended product stability and condition the hair as well as compositions specifically designed to condition the hair.

Therefore, one important aspect of the present invention is to provide a shampoo-conditioner composition that cleans the hair and conditions the hair in a single application.

Another aspect of the present invention is to provide a phase stable, aqueous shampoo-conditioner composition comprising a cleansing surfactant; a water-insoluble primary amine having about 14 to about 22 carbon atoms; and a sufficient amount of a suitable acid.

Another aspect of the present invention is to provide a new and improved shampoo-conditioner composition, comprising a cleansing surfactant selected from the group consisting of a nonionic surfactant, an amphoteric surfactant or a combination thereof, a water-insoluble primary amine and a sufficient amount of a suitable acid, that cleans the hair as well as anionic surfactant-based shampoos and that conditions the hair as well as a conditioning composition including a silicone conditioner.

Still another aspect of the present invention is to provide a new and improved shampoo-conditioner composition including about 5% to about 30% of a cleansing surfactant; about 0.5% to about 5% of a water-insoluble primary amine including about 14 to about 22 carbon atoms; and (c) a sufficient amount of an inorganic mineral acid, an aliphatic carboxylic acid including up to about 5 carbon atoms, or a combination thereof, such that 30 mole percent or more of the primary amine is neutralized and such that the composition has a pH of about 4 to about 8. Optionally, the hair shampoo composition further includes 0% to 2% by weight of a water-soluble quaternary ammonium compound having one long carbon chain of about 12 to about 18 carbon atoms, a water-soluble amine at pH 6 or a mixture thereof.

Another aspect of the present invention is to provide a phase-stable shampoo-conditioner composition having a pH of about 4 to about 8 that is capable of cleaning and conditioning the hair, and that is capable of generating a consumer-acceptable foam height, wherein the composition is essentially free of an anionic surfactant and is essentially free of a silicone or a hydrocarbon conditioning agent.

Another aspect of the present invention is to provide a method of shampooing and conditioning hair by contacting the hair with a composition having a pH of about 4 to about 8, said composition comprising a nonionic and/or amphoteric cleansing surfactant; a water-insoluble primary amine having about fourteen to about twenty-two carbon atoms; a sufficient amount of an inorganic mineral acid, an aliphatic carboxylic acid having up to about 5 carbon atoms, or a combination thereof; and water.

BRIEF DESCRIPTION OF THE DRAWINGS

The above and other aspects and advantages of the present invention will become apparent from the following detailed description of the preferred embodiments illustrated in the accompanying figures illustrating the enhanced foaming and conditioning properties achieved using the method and composition of the present invention, wherein.

DETAILED DESCRIPTION OF THE PREFERRED EMBODIMENTS

Figure 1:
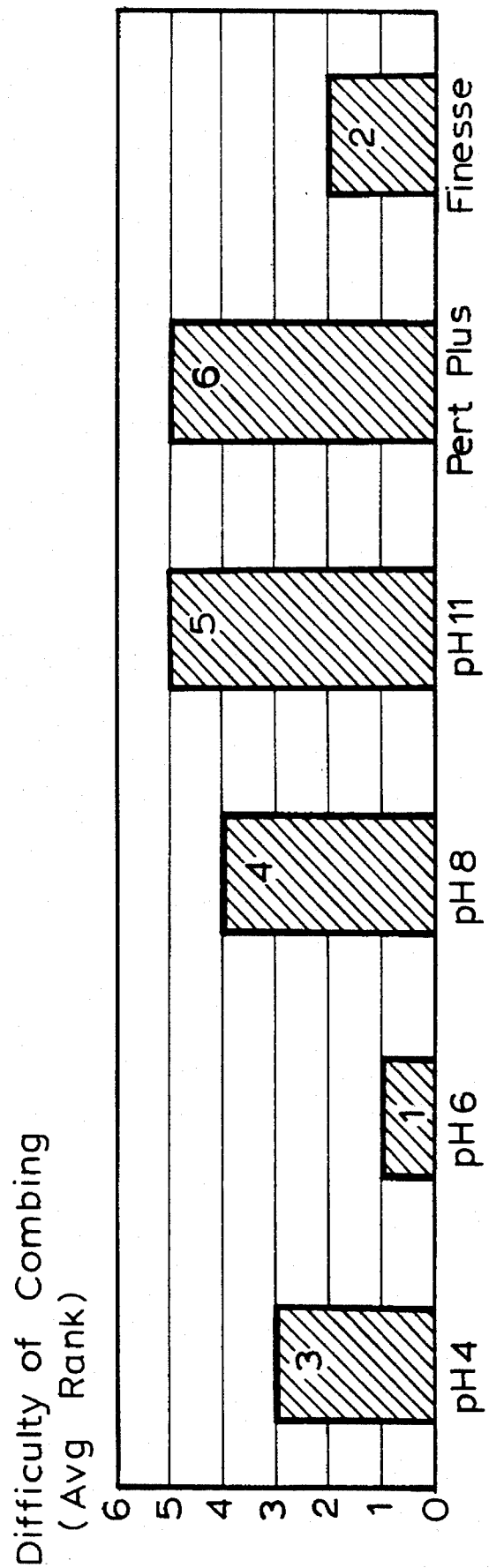
FIG. 1 is a bar graph comparing the combing difficulty of hair shampooed with a composition of the present invention over the pH range of about 4 to about 11 and to a commercial shampoo-conditioner (PERT PLUS) and a commercial conditioner (FINESSE)

A shampoo-conditioner composition of the present invention comprises a cleansing surfactant, a water-insoluble primary amine, a sufficient amount of a suitable acid, and a carrier comprising water. The cleansing surfactant is selected from the group consisting of a nonionic surfactant, an amphoteric surfactant, and combinations thereof. The cleansing surfactant is water-soluble and generates a sufficient foam height for consumer acceptance. In accordance with an important feature of the present invention, the primary amine includes about 14 to about 22 carbon atoms; and the acid is selected from the group consisting of an inorganic mineral acid, an aliphatic carboxylic acid including up to about 5 carbon atoms, and combinations thereof, and is present in a sufficient amount to neutralize at least 30 mole percent, or synonymously 30 mole percent or more, of the primary amine and to provide a composition having a pH of about 4 to about 8. The aqueous shampoo-conditioner composition optionally includes 0% to about 2% by weight of a quaternary ammonium compound having one long carbon chain of from about 12 to about 18 carbon atoms, a water-soluble amine at pH 6 or a mixture thereof.

The shampoo-conditioner composition is essentially free of an anionic surfactant and of a silicone or hydrocarbon conditioning agent, but unexpectedly exhibits a consumer-acceptable foam height, effectively cleans and conditions hair and is phase stable.

The cleansing surfactant used in the composition and method of the present invention is selected from the group consisting of a nonionic surfactant, an amphoteric surfactant and mixtures thereof, wherein the cleansing surfactant is water-soluble and generates a consumer-acceptable foam level, and wherein the nonionic surfactant has an HLB (hydrophilic-lipophilic balance) of at least about 12. A nonionic or amphoteric cleansing surfactant is useful in the shampoo-conditioner composition because such surfactants effectively clean the hair, do not interact adversely with cationic components present in the composition, generate a high foam height that consumers equate with cleaning efficiency, and are mild.

A preferred nonionic surfactant includes a hydrophobic moiety, such as an aromatic or aliphatic moiety having a carbon chain including from about 8 carbon atoms to about 30 carbon atoms, and particularly from about 12 carbon atoms to about 20 carbon atoms; and further includes a sufficient number of hydrophilic moieties, such as alkylene oxide moieties, like ethoxy or propoxy moieties. The hydrophobic carbon chain typically is etherified with a sufficient amount of ethylene oxide and/or propylene oxide to provide a water-soluble nonionic surfactant. A nonionic surfactant useful in the present invention has an HLB (hydrophilic lipophilic balance) of at least about 12, preferably from about 12 to about 24, and to achieve the full advantage of the present invention from about 12 to about 20. The HLB value for a surfactant having a particular hydrophobic moiety varies with the amount of ethylene oxide and/or propylene oxide in the surfactant.

The HLB of a nonionic surfactant can be experimentally determined by a person skilled in the art using known methods or can be approximated by the expression HLB= E/5, wherein E is the weight percentage of alkylene oxide in the surfactant. The HLB values for commercially-available nonionic surfactants typically are published in well-known reference sources, such as *MCCUTCHEON'S DETERGENTS AND EMULSIFIERS, NORTH AMERICAN EDITION, 1993 ANNUAL*, pages 229–246, published by McCutcheon Division, MC Publishing Co., Glen Rock, N.J., incorporated herein by reference.

In addition to being water-soluble and having an HLB of at least about 12, a suitable nonionic surfactant generates a sufficient foam height for consumer acceptance. Consumers equate high foam height with good cleaning, and therefore the esthetic effect of high foam height is necessary for a commercially-successful product. Accordingly, a nonionic surfactant that provides a shampoo-conditioner composition having an initial foam height of at least 160 milliliters (ml) (i.e., synonymously expressed as 160 milliliters or greater), and preferably at least 200 ml, and a foam height after five minutes of 160 ml or greater, and preferably 190 ml or greater, in the absence of any cationic or anionic surfactants in the shampoo-conditioner composition, is useful in the present invention.

The foam height of the shampoo-conditioner composition is determined by adding 0.2 grams (g) of the composition to 100 ml tap water in a stoppered 500 ml graduated cylinder. The graduated cylinder then is completely inverted 10 times. The foam height is measured within 5 seconds for initial foam height, and is measured again after 5 minutes. The reported foam heights include the 100 ml of water.

Nonionic surfactants are well-known materials and have been used in cleansing compositions. Therefore, suitable nonionic surfactants include, but are not limited to, compounds in the classes known as alkanolamides, block copolymers of ethylene and propylene, ethoxylated alcohols, ethoxylated alkylphenols, alkyl polyglycosides and mixtures thereof.

In particular, the nonionic surfactant can be an ethoxylated alkylphenol, i.e., a condensation product of an alkylphenol having an alkyl group containing from about 6 to about 12 carbon atoms in either a straight chain or branched chain configuration with ethylene oxide, the ethylene oxide being present in an amount equal to at least about 8 moles ethylene oxide per mole of alkylphenol. Examples of compounds of this type include nonylphenol condensed with about 9.5 moles of ethylene oxide per mole of phenol; dodecylphenol condensed with about 12 moles of ethylene oxide per mole of phenol; dinonylphenol condensed with about 15 moles of ethylene oxide per mole of phenol; octylphenol condensed with about ten moles of ethylene oxide per mole of phenol; and diisooctyl phenol condensed with about 15 moles of ethylene oxide per mole of phenol. These ethoxylated alkylphenol nonionic surfactants are designated as in the *CTFA INTERNATIONAL COSMETIC INGREDIENT DICTIONARY, FOURTH ED.*, The Cosmetic Toiletry and Fragrance Association, Washington, D.C. (1991) (hereinafter the *CTFA Dictionary*) as octoxynols, nonoxynols, dodoxynols and nonyl nonoxynols. Particular ethoxylated alkylphenols include dodoxynol-9, dodoxynol-12, nonoxynol-10, nonoxynol-18, nonoxynol-30, nonyl nonoxynol-10, nonyl nonoxynol-49, octoxynol-10 and octoxynol-16.

The ethoxylated alcohols, i.e., condensation products of aliphatic alcohols having about 8 to about 22 carbon atoms with about 5 to about 25 moles of ethylene oxide, also are useful nonionic surfactants. The alkyl chain of the aliphatic alcohol can be either straight or branched, primary or secondary. Preferred nonionic surfactants are the condensation products of alcohols having an alkyl chain containing about 10 to about 20 carbon atoms with from about 6 to about 10 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from about 10 to about 14 carbon atoms) with about 9 moles of ethylene oxide. Numerous ethoxylated alcohols (and ethoxylated alkylphenols) are listed in the *CTFA COSMETIC INGREDIENT HANDBOOK, FIRST EDITION*, The Cosmetic, Toiletry and Fragrance Association (1988) (hereinafter the *CTFA Handbook*), pages 4–6, incorporated herein by reference. Exemplary ethoxylated alcohols include, but are not limited to, $C_{11-15}$ pareth-12, laneth-15, oleth-12, beheneth-20, $C_{12-15}$ pareth-12, ceteareth-20, ceteth-16, coceth-8, isoceteth-20, isosteareth-10, laureth-13, octyldodeceth-20, oleth-10, trideceth-15 and steareth-16.

Especially preferred nonionic surfactants are the alkyl polyglycosides. Alkyl polyglycosides are disclosed in numerous patents, such as for example Llenado U.S. Pat. No. 4,565,647. The alkyl polyglycosides have a hydrophobic group containing from about 6 to about 30 carbon atoms, preferably from about 10 to about 16 carbon atoms, and a polysaccharide, e.g., a polyglycoside, hydrophilic group containing from about 1.5 to about 10, preferably from about 1.5 to about 3, and most preferably from about 1.6 to about 2.7, saccharide units. Any reducing saccharide containing 5 or 6 carbon atoms can be used, e.g., glycose, galactose and galactosyl moieties can be substituted for the glucosyl moieties.

Optionally, a polyalkylene oxide chain can join the hydrophobic moiety and the polysaccharide moiety. The preferred alkylene oxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a saturated, straight chain alkyl group. The alkyl group can contain up to about 3 hydroxy groups, and the polyalkylene oxide chain can contain up to about 10, preferably less than 5, alkylene oxide moieties. Suitable alkyl polysaccharides are octyl, nonyl, decyl, undecyl, dodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, galactoses, and mixtures thereof. Suitable mixtures include coconut alkyl di-, tri-, tetra-, and pentaglucosides and tallow alkyl tetra-, penta-, and hexaglucosides.

The preferred alkyl polyglycosides have the formula

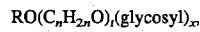

$$RO(C_nH_{2n}O)_t(glycosyl)_x$$

wherein R is selected from the group consisting of alkyl, alkylphenyl, hydroxyalkyl, hydroxyalkylphenyl, and mixtures thereof wherein the alkyl group contains from about 10 to about 18, preferably from about 12 to about 14, carbon atoms; n is 2 or 3; t is a number from 0 to about 10, preferably 0; and x is a number from about 1.3 to about 10, preferably from about 1.3 to about 3, most preferably from about 1.3 to about 2.7. The glycosyl preferably is derived from glucose. Especially useful nonionic surfactants are the alkyl polyglycosides like decyl polyglucose and lauryl polyglucose, available commercially as PLANTAREN™ 2000 and PLANTAREN™ 1300 from Henkel Corporation, Emery Group Cospha, Ambler, Pa.

The laurate esters of sorbitol condensed with at least about 20 moles of ethylene oxide also are useful nonionic surfactants. Exemplary nonionic surfactants in this class include polysorbate 20, polysorbate 21, polysorbate 40, polysorbate 60, polysorbate 61, polysorbate 65, polysorbate 80, polysorbate 81, and polysorbate 85, as designated in the *CTFA Dictionary*.

As will be demonstrated in detail hereinafter, a nonionic surfactant having an HLB of at least about 12 and the ability to generate an initial composition foam height of at least about 160 ml is useful in the present invention. Therefore, in addition to the above-listed classes of nonionic surfactants and the above-listed specific nonionic surfactants, numerous other nonionic surfactants having an HLB of at least about 12 (i.e., about 12 or more) and the ability to generate an initial foam height of 160 ml or greater also are useful in the present shampoo-conditioner composition.

For example, the nonionic surfactant included in the shampoo-conditioner composition of the present invention also can be an ether of a polyol and a sugar; fatty acid alkanolamide; a polyethylene glycol; or a condensation product of ethylene oxide with a long chain amide. These nonionic surfactants, as well as numerous others not cited herein, are well known to person skilled in the art and are fully described in the literature, such as *McCUTCHEON'S DETERGENTS AND EMULSIFIERS, NORTH AMERICAN EDITION, 1993 ANNUAL*, published by McCutcheon Division, MC Publishing Co., Glen Rock, N.J.

In particular, a nonionic alkanolamide can be included in the composition, alone or in combination with another nonionic surfactant. Suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

In conjunction with, or in place of, the nonionic surfactant, an amphoteric surfactant can be included in a present shampoo-conditioner composition. An amphoteric surfactant cleans the hair and generates sufficient foam for consumer acceptance. However, a nonionic surfactant is preferred because a nonionic surfactant generates a greater initial foam than an amphoteric surfactant in the presence of the primary amine. Suitable classes of amphoteric surfactants included in the present invention include, but are not limited to, betaines, hydroxypropylsultaines and combinations thereof. Examples of specific amphoteric surfactants include, but are not limited to, cocamidopropyl betaine, lauramidopropyl betaine, cocooleamidopropyl betaine, coco betaine, oleyl betaine, cocamidopropyl hydroxysultaine, tallowamidopropyl hydroxysultaine and dihydroxyethyl tallow glycinate or combinations thereof. In general, however, any amphoteric surfactant known and used in the art of hair shampoos can be included in a composition of the present invention.

In accordance with an important feature of the present invention, a nonionic surfactant, an amphoteric surfactant or a mixture thereof is present in the shampoo-conditioner composition in an amount of about 5% to about 30%, and preferably about 8% to about 20%, by weight of the composition. If the cleansing surfactant is present in an amount less than 5% by weight of the composition, then the hair is not sufficiently cleaned when contacted with a shampoo-conditioner composition of the present invention. Therefore, the cleansing surfactant, or combination of cleansing surfactants, generally is included in a hair shampoo composition of the present invention in a preferred amount ranging from about 8% to about 20% by weight of the composition, and to achieve the full advantage of the present invention, from about 10% to about 20% by weight of the composition. Furthermore, surprisingly and unexpectedly, even when a low amount of cleansing surfactant is included in the composition, such as from about 5% to about 10% by weight of the composition, the presence of the primary amine does not adversely affect the generation of a sufficient and stable foam height for consumer acceptance.

In accordance with another important feature of the present invention, the shampoo-conditioner composition is essentially free of an anionic surfactant. The phrase "essentially free" is defined as meaning that an anionic surfactant is not intentionally added to the composition, but may be present in small amounts as a contaminant or as a by-product in an ingredient of the composition. Accordingly, an anionic surfactant can be present in a shampoo-conditioner composition in an amount of 0.2% or less, by weight of the composition. The absence of an anionic surfactant precludes anionic-cationic interactions in the composition. Surprisingly, however, a consumer-acceptable foam height is generated even in the absence of a high-foaming anionic surfactant.

In accordance with another important feature of the present invention, the shampoo-conditioner composition also is essentially free of a silicone conditioning agent or a hydrocarbon conditioning agent. The term "essentially free" has been defined above with respect to the presence of an anionic surfactant. Such conditioning agents often are included in shampoo-conditioner compositions to sufficiently condition the hair. The present shampoo-conditioner composition however sufficiently conditions shampooed hair without the need for such water-insoluble conditioning agents.

Surprisingly, the present shampoo-conditioner compositions, including a primary amine and a sufficient amount of a suitable acid, and, optionally, a quaternary ammonium compound including one long carbon chain, condition hair essentially equally to a composition designed specifically to condition previously-shampooed hair. Such a result is unexpected because shampoo-conditioner compositions are inferior conditioners compared to specifically-designed conditioning compositions.

In addition to the cleansing surfactant, a shampoo-conditioner composition of the present invention also includes a primary amine having about 14 to about 22 carbon atoms. The primary amine is water-insoluble, is homogeneously dispersed throughout the composition for at least the expected life of the product, does not adversely affect the foaming or cleaning properties of the shampoo-conditioner, and effectively conditions the hair.

Preferably, the primary amine includes about 16 to about 22 carbon atoms, and to achieve the full advantage of the present invention from about 16 to about 20 carbon atoms. A primary amine including 12 or fewer carbon atoms is sufficiently water-soluble such that the amine is rinsed from the hair, and therefore does not condition the hair. The water-insoluble primary amine is dispersed in the composition by including a sufficient amount of a suitable acid in the composition.

The primary amine is present in the shampoo-conditioner composition in an amount of about 0.5% to about 5%, and preferably about 1% to about 5%, by weight of the composition; the acid is present in the shampoo-conditioner composition in a sufficient amount such that the amine is neutralized about 30 mole percent or more, and such that the composition has a pH of about 4 to about 8. Below about 0.5% by weight, the primary amine is not present in a sufficient amount to condition the hair. Above about 5% by weight, the primary amine conditions hair to such an extent that the hair feels greasy.

The term "at least 30 mole percent" is defined by its common English meaning which is known and used by those skilled in the art as "at a minimum of 30 mole percent" or "30 mole percent or greater". The terms "at a minimum of 30 mole percent" "30 mole percent or greater" and "at least 30 mole percent" are used synonymously.

The alkyl group of the primary amine can be derived from a fatty acid, and therefore does not have to be solely, or primarily, of one chain length, i.e., the long chain need not be derived only from cetyl ($C_{16}$) or stearyl ($C_{18}$). Rather, a primary amine wherein the alkyl group is a mixture of lengths can be used, as long as the primary amine is water insoluble and includes about 14 to about 22 carbon atoms. Such amine compounds are prepared conveniently from naturally occurring materials, such as tallow, soya oil and the like, or from synthetically produced mixtures.

In particular, a primary amine including about 14 to about 22 carbon atoms typically is a solid compound at room temperature. It should be understood however that a commercial primary amine having about 14 to about 22 carbon atoms as the predominant chain length also can include a minor amount of an amine having a carbon chain of fewer than 14 carbon atoms. A minor amount of a primary amine having carbon chain including less than 14 carbon atoms, e.g., up to about 5% by weight of the primary amine present in the composition, does not adversely affect the composition. The primary amines therefore usually are solid compounds at room temperature, and are water-insoluble compounds exhibiting a water solubility of 0.5 g or less per 100 ml of water.

When the primary amine is sufficiently neutralized by the acid, the primary amine is dispersed throughout the shampoo-conditioner composition, but still is sufficiently water insoluble to deposit on and condition the hair during shampooing. The primary amine is effectively suspended in the shampoo-conditioner composition at least for the expected life of the product, e.g., about one year, without adversely affecting the other properties of the shampoo-conditioner composition, like foam height generation.

Specific primary amines useful in a shampoo-conditioner composition of the present invention include, but are not limited to, $C_{20-22}$ amine, soya amine, hydrogenated tallow amine, stearyl amine, tallow amine, oleyl amine, hexadecylamine, octadecylamine, and combinations thereof.

In addition to a primary amine and a cleansing surfactant, a present shampoo-conditioner composition also includes a sufficient amount of a suitable acid to neutralize at least about 30 mole percent of the primary amine and to provide a composition having a pH of about 4 to about 8. A sufficient amount of an inorganic mineral acid, an aliphatic carboxylic acid including up to about 5 carbon atoms, or a combination thereof is present to neutralize the primary amine to such a degree that the primary amine, both neutralized and unneutralized, is dispersed homogeneously throughout the composition, i.e., at least 30 mole percent or, synonymously, 30 mole percent or more, of the amine is neutralized.

In addition, a sufficient amount of an acid is added to provide a composition pH of about 4 to about 8. If excess acid is present in the composition, the hair is neutralized to a sufficient extent during shampooing such that the primary amine is not substantive to the hair, but is rinsed from the hair. Accordingly, the primary amine does not condition the hair during shampooing. If an insufficient amount of acid is present in the composition, composition pH may be sufficiently high to cause irritation and the primary amine is not effectively deposited on the hair.

The acid used to neutralize the amine compound is of sufficient acid strength to neutralize a free amine nitrogen. Such acids include, but are not limited to, the inorganic mineral acids, like hydrochloric acid, sulfuric acid, nitric acid, phosphoric acid, and mixtures thereof. In addition, an aliphatic carboxylic acid including up to about 5 carbon atoms can be used to neutralize the primary amine. Preferably, the aliphatic carboxylic acid is a saturated aliphatic acid. An aliphatic carboxylic acid including more than about 5 carbon atoms provides a composition having decreased esthetic properties compared to compositions including a saturated acid having about 5 or fewer carbon atoms. Examples of suitable aliphatic carboxylic acids include, but are not limited to, acetic acid, lactic acid, citric acid, tartaric acid, propionic acid, butyric acid, pentanoic acid, glycolic acid, and mixtures thereof.

In addition to the above-described essential ingredients, other common cosmetic components and additives can be included in a shampoo-conditioner composition of the present invention to impart desirable or esthetic properties, as long as the basic properties of the shampoo-conditioner composition are not adversely affected. Such optional cosmetic components and additives include, but are not limited to, fragrances, dyes, hair colorants, opacifiers, pearlescing agents, thickeners, inorganic salts, humectants, hydrotropes, foam stabilizers, solubilizers, preservatives, water softening agents, buffers and the like. These optional components and additives usually are present in weight percentages of 0% up to about 5% by weight of the shampoo-conditioner composition each, and usually 0% to about 20% by weight of the shampoo-conditioner composition in total.

In particular, a quaternary ammonium compound can be added to the shampoo-conditioner composition to enhance the foaming properties of the composition. The quaternary ammonium compound is water soluble and has one long carbon chain of about 12 to about 18, and preferably about 14 to about 18, carbon atoms. The water-soluble quaternary ammonium compound is present in the shampoo-conditioner composition in an amount of 0% to about 2%, and preferably about 0.1% to about 1%, by weight of the composition.

The carbon chain of the quaternary ammonium compound also can include, in addition to, or in replacement of, carbon and hydrogen atoms, ether linkages or similar water-solubilizing linkages. The remaining three substituents of the quaternary nitrogen of the quaternary ammonium compound can be phenyl; benzyl; or short chain alkyl or hydroxyalkyl groups, such as methyl, ethyl, hydroxymethyl or hydroxyethyl groups; or combinations thereof, either of the same or of different identity, as long as the quaternary ammonium compound is water-soluble.

Therefore, the water-soluble quaternary ammonium compound can be depicted by the following general structural formula:

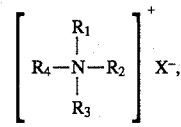

wherein $R_1$ is an alkyl group including from about 12 to about 18 carbon atoms; $R_2$ and $R_3$, independently, are selected from the group consisting of a methyl group, an ethyl group, a hydroxymethyl group and a hydroxyethyl group; $R_4$ is selected from the group consisting of a benzyl group, a methyl group, an ethyl group, a hydroxymethyl group and a hydroxyethyl group; and X is selected from the group consisting of chloride, methosulfate, ethosulfate and nitrate. The quaternary nitrogen of the water-soluble quaternary ammonium compound also can be included in a heterocyclic nitrogen-containing moiety, such as morpholine or pyridine. Furthermore, the anion of the quaternary ammonium compound can be any common anion, in addition to those listed above, such as bromide, tosylate, acetate, or phosphate, as long as the quaternary ammonium compound is water soluble.

Water-soluble quaternary ammoninum compounds having a quaternary nitrogen atom and one long carbon chain including about 12 to about 18 carbon atoms include a broad range of compounds. However, the water-soluble quaternary ammonium compounds generally can be divided into groups based upon the structure of the substituents present on the quaternary nitrogen atom, i.e., (a) compounds having one long carbon chain and three identical or different short chain alkyl or hydroxyalkyl groups containing one or two carbon atoms, i.e, methyl, ethyl, hydroxymethyl or hydroxyethyl groups; (b) compounds having one long carbon chain, one benzyl group and two identical or different short chain alkyl or hydroxyalkyl groups having one or two carbon atoms; and (c) compounds having one long carbon chain, and one organic heterocyclic nitrogen-containing moiety, like morpholine or pyridine, and none or one short chain alkyl or hydroxyalkyl group having one or two carbon atoms.

Therefore, in accordance with an important feature of the present invention, the following water-soluble quaternary ammonium compounds are exemplary, but not limiting, compounds that can be used in the method and composition of the present invention:

| | |
|---|---|
| Lauryltrimethylammonium chloride | (Laurtrimonium chloride); |
| Stearyltri(2-hydroxyethyl) ammonium chloride | (Quaternium-16); |
| Lauryldimethylbenzylammonium chloride | (Lauralkonium chloride); |
| Oleyldimethylbenzylammonium chloride | (Olealkonium chloride); |
| Stearyltrimethylammonium chloride | (Steartrimonium chloride); |
| Cetyldimethylbenzylammonium chloride | (Cetalkonium chloride); |
| Alkyldimethylbenzylammonium chloride | (Benzalkonium chloride); |
| Tallowtrimethylammonium chloride | (Tallowtrimonium chloride); |
| Laurylpyridinium chloride | (Laurylpyridinium chloride); |
| Cetylpyridinium chloride | (Cetylpyridinium chloride); |
| N-(soya alkyl)-N,N,N-trimethyl ammonium chloride | (Soyatrimonium chloride); |
| Cetyltrimethylammonium chloride | (Cetrimonium chloride); |
| Myristyltrimethylammonium chloride | (Mytrimonium chloride); |
| Polyoxyethylene(2)-cocomonium chloride | (PEG-2 Cocomonium chloride); |
| Methylbis(2-hydroxyethyl)cocoammonium chloride | (PEG-2 Cocoyl Quaternium-4); |
| Methylpolyoxyethylene(15)-cocoammonium chloride | (PEG-15 Cocoyl Quaternium-4); |
| Methylbis(2-hydroxyethyl)octadecylammonium chloride | (PEG-2 Stearyl Quaternium-4); |
| Methylpolyoxyethylene-(15)octadecylammonium chloride | (PEG-15 Stearyl Quaternium-4); |
| Methylbis(2-hydroxyethyl)-oleylammonium chloride | (PEG-2 Oleyl Quaternium-4); |
| Methylpolyoxyethylene-(15) oleylammonium chloride | (PEG-15 Oleyl Quaternium-4); | wherein the name in parenthesis is the compound designation given by the Cosmetic, Toiletry and Fragrance Association, Inc. in the *CTFA Dictionary*. Other quaternary ammonium compounds are listed in the *CTFA Handbook*, pages 40–42, incorporated herein by reference.

A water-soluble amine can be included in the shampoo-conditioner composition in place of, or in combination with, the water-soluble quaternary ammonium compound to enhance the foaming properties of the composition. The amine is water soluble at a composition pH of about 6 and can be a primary, secondary or tertiary amine, wherein the amine has one long carbon chain. For water-soluble primary amines, the long carbon chain contains about 8 to about 12 carbon atoms. Primary amines that have an unsaturated carbon chain containing about 8 to about 18 carbon atoms also can be used as the water-soluble amine. For water-soluble secondary and tertiary amines, the long carbon chain contains about 8 to about 16 carbon atoms. The water-soluble amine is present in an amount of 0% to about 2%, and preferably about 0.1% to about 1.2%, by weight of the composition.

Examples of water-soluble amines that can be added to the shampoo-conditioner compositions to enhance foam generation include, but are not limited to, 2-ethylhexylamine, dodecylamine, dodecyl dimethylamine, hexadecyl dimethylamine, oleyl dimethylamine, cetyl dimethylamine, myristyl dimethylamine, oleyl amine, and cocamine. Other water-soluble amines are listed in the *CTFA Handbook*, pages 13–14, incorporated herein by reference.

The carrier of the shampoo composition is predominantly water, but nonaqueous solvents also can be included to help solubilize composition ingredients that are not sufficiently soluble in water or to adjust the viscosity of the composition. Suitable solvents include polyols, like glycerol; glycols, like ethylene glycol, propylene glycol and hexylene glycol; or mixtures thereof. The optional nonaqueous solvents should not adversely affect the ability of the composition to clean and condition the hair, or adversely affect consumer appeal of the composition, such as by decreasing the foam height. A nonaqueous solvent can be present in a shampoo-conditioner composition of the present invention in an amount of 0% up to about 5% by weight of the composition.

To achieve the full advantage of the present invention, the shampoo composition is a moderately viscous mixture, e.g., having a viscosity in the range of about 1000 cps (centipoises) to about 15,000 cps, that is stable indefinitely at temperatures normally found in commercial product storage and shipping. A shampoo-conditioner composition of the present invention generally is a dispersion that resists phase separation at a temperature of about 20° C. to about 25° C. essentially indefinitely. The shampoo-conditioner compositions also have demonstrated phase stability at temperatures normally found in commercial product storage and shipping to remain unaffected for periods of one year or more.

In accordance with the method of the present invention, several shampoo-conditioner compositions were prepared, then applied to human hair, to demonstrate the improved ability of a shampoo-conditioner composition to clean and condition the hair. It has been demonstrated that to maximize hair conditioning, the shampoo-conditioner composition includes the primary amine and the acid in sufficient amounts such that at least 30%, and preferably at least 50% (i.e., 50% or more) by weight of the amine is neutralized, and such that the composition has a pH of about 4 to about 8, and preferably about 5 to about 7.

A shampoo-conditioner composition including only free primary amine, i.e., a primary amine not neutralized with an acid, did not condition hair, demonstrated poor foaming properties and underwent a phase separation relatively rapidly, such as in less than 24 hours. Accordingly, the acid-neutralized primary amine is dispersed throughout the composition and helps suspend the unneutralized amine. The neutralized and unneutralized primary amine condition the hair.

Furthermore, laboratory tests have shown that hair shampooed with a composition of the present invention is effectively cleaned and that the hair is effectively conditioned. As will be demonstrated in more detail hereinafter, the present shampoo-conditioner compositions condition the hair as well as a leading commercial composition which is specifically designed to condition hair.

condition shampooed hair. Accordingly, a composition including a combination of a neutralized amine and an anionic surfactant does not satisfactorily condition shampooed hair.

| Ingredient | EXAMPLE 6[1] | EXAMPLE 7 | EXAMPLE 8 | EXAMPLE 9 |
|---|---|---|---|---|
| PLANTAREN ™ 2000[6] | — | 11.25 | 11.25 | 11.25 |
| MIRANOL C2M[7] | 15.0 | 3.75 | 3.75 | 3.75 |
| ADOGEN 141D[3] | 5.0 | 1.0 | 3.0 | 5.0 |
| Deionized water | q.s. | q.s. | q.s. | q.s. |

[6] Decyl polyglucose nonionic surfactant, available as a 50% active solution from Henkel Corp., Emery Group, Cospha, Ambler, PA.;
[7] Cocoamphodipropionic acid amphoteric surfactant, available from Rhone-Poulenc, Cranbury, NJ.

To demonstrate the new and unexpected results achieved by the method and composition of the present invention, the following Examples 1 through 30 were prepared by an identical method, wherein the cleansing surfactant, or blend of surfactants, and water were added to a first vessel, and the resulting mixture was heated to about 50° to about 70° C. under moderate agitation. The primary amine was melted in a second vessel, and the melted primary amine then was added to the mixture in the first vessel under continued agitation. The resulting mixture was maintained at about 70° C. and agitated for about 30 to about 90 minutes to homogenize the mixture. Then, the homogeneous mixture was cooled to room temperature. Next an acid (either citric acid or hydrochloric acid) was added to the homogeneous mixture to provide a shampoo-conditioner composition having a pH of about 6.

The compositions of Examples 6–9 each include a primary amine and either an amphoteric surfactant or a combination of an nonionic surfactant and an amphoteric surfactant. The compositions of Examples 6–9 were screened for an ability to condition hair by shampooing hair with a composition, then qualitatively examining the hair for conditioning properties. Each composition of Examples 6–9 effectively conditioned shampooed hair, with the degree of conditioning increasing in direct proportion to the amount of primary amine in the composition. In contrast, the compositions of Examples 1–3, which include the same primary

| Ingredient | EXAMPLE 1[1] | EXAMPLE 2 | EXAMPLE 3 | EXAMPLE 4 | EXAMPLE 5 |
|---|---|---|---|---|---|
| Sodium lauryl sulfate[2] | 18.0 | 18.0 | 18.0 | 18.0 | 18.0 |
| Cocamide DEA | 3.0 | 3.0 | 3.0 | 3.0 | 3.0 |
| Sodium chloride | 2.0 | 2.0 | 2.0 | 2.0 | 2.0 |
| ADOGEN 141D[3] | 1.0 | 3.0 | 5.0 | — | — |
| ADOGEN 240[4] | — | — | — | 3.0 | — |
| ARMEEN DM18D[5] | — | — | — | — | 3.0 |
| Deionized water | q.s. | q.s. | q.s. | q.s. | q.s. |

[1] Percent by weight of ingredient in the composition;
[2] SLS, added as a 30% by weight active solution;
[3] Distilled stearyl amine, a primary amine available from Sherex Chemical Co., Dublin, Ohio;
[4] Di(hydrogenated tallow)amine, a secondary amine available from Sherex Chemical Co., Dublin, Ohio;
[5] N,N-dimethyloctadecylamine, a tertiary amine available from Akzo Chemicals, Inc., Chicago, Illinois.

The compositions of Examples 1–5, each including an anionic surfactant, are comparative examples. The compositions of Examples 1–5 were screened for an ability to condition hair by shampooing hair with a composition, then qualitatively examining the hair for conditioning properties. The composition of Example 5 mildly conditioned shampooed hair. The compositions of Examples 1–4 did not amine (i.e., stearyl amine) as the composition of Examples 6–9 and an anionic surfactant, failed to condition the hair. Therefore, a shampoo-conditioner composition comprising a primary amine, a sufficient amount of an acid, and a nonionic and amphoteric surfactant (or an amphoteric surfactant) effectively cleans and conditions the hair.

| Ingredient | EXAMPLE 10[1] | EXAMPLE 11 | EXAMPLE 12 |
|---|---|---|---|
| PLANTAREN ™ 2000[6] | 7.5 | 7.5 | 7.5 |
| Sodium lauryl ether sulfate[8] | 7.5 | 7.5 | 7.5 |
| ADOGEN 141D[3] | 1.25 | 2.5 | 4.0 |
| Deionized water | q.s. | q.s. | q.s. |

[8] Added as a 30% by weight active solution.

The compositions of Examples 10–12 include a primary amine and a blend of a nonionic and an anionic surfactant. The compositions were screened for an ability to condition hair by shampooing the hair with a composition, then qualitatively examining the hair for conditioning properties. Hair shampooed with a composition of Examples 10–12 was not conditioned, even though the composition of Example 12 includes a relatively high level of primary amine. Accordingly, the neutralized and unneutralized primary amine is unable to condition hair when an anionic surfactant is present in the composition. In contrast, the presence of nonionic and amphoteric surfactants in the shampoo-conditioning composition (e.g., Examples 7–9), in the absence of an anionic surfactant, does not reduce the ability of the primary amine to condition the hair.

The compositions of Examples 19–24 include a nonionic surfactant, a primary amine, an acid, and an optional quaternary ammonium compound. The quaternary ammonium compound increased the foam height generated by the compositions. The compositions were screened for an ability to condition hair by Shampooing hair with a composition, then qualitatively examining the hair for conditioning properties. Hair shampooed with a composition of Examples 19–24 was effectively conditioned, thereby illustrating that the quaternary ammonium compound does not adversely affect the shampoo-conditioner composition.

| Ingredient | EXAMPLE 13[1] | EXAMPLE 14 | EXAMPLE 15 | EXAMPLE 16 | EXAMPLE 17 | EXAMPLE 18 |
|---|---|---|---|---|---|---|
| PLANTAREN ™ 2000[6] | 17.5 | 17.5 | 15.0 | 15.0 | 15.0 | 15.0 |
| Cocamide DEA | — | — | — | 2.5 | 2.5 | 2.5 |
| ADOGEN 141D[3] | 5.0 | 10.0 | — | 1.0 | 2.0 | 4.0 |
| ARMEEN DM18D[5] | — | — | 3.0 | — | — | — |
| Deionized water | q.s. | q.s. | q.s. | q.s. | q.s. | q.s. |

The compositions of Examples 13–18 include a combination of either a nonionic surfactant (Examples 13–14) or a nonionic surfactant blend (Examples 16–18) and a primary amine, or a nonionic surfactant and tertiary amine (Example 15). The compositions were screened for an ability to condition hair by shampooing hair with a composition, then qualitatively examining the hair for conditioning properties. Hair shampooed with a composition of Example 13–18 was conditioned, however, the composition of Example 15 did not condition the hair as well as the compositions of Examples 13–14 and 16–18.

| Ingredient | EXAMPLE 19[1] | EXAMPLE 20 | EXAMPLE 21 | EXAMPLE 22 | EXAMPLE 23 | EXAMPLE 24 |
|---|---|---|---|---|---|---|
| PLANTAREN ™ 2000[6] | 15.0 | 15.0 | 15.0 | 15.0 | 15.0 | 15.0 |
| BARQUAT CT 429[9] | 0.3 | 0.6 | 0.6 | 0.3 | 0.3 | 0.3 |
| Cocamide DEA | 1.5 | 3.0 | — | 1.25 | 1.25 | 1.25 |
| ADOGEN 141D[3] | 1.5 | 5.0 | 5.0 | 1.0 | 3.0 | 5.0 |
| Deionized water | q.s. | q.s. | q.s. | q.s. | q.s. | q.s. |

[9] Cetrimonium chloride, a quaternary ammonium compound available as a 29% active material from Lonza, Inc., Fairlawn, NJ.

| Ingredient | EXAMPLE 25[1] | EXAMPLE 26 | EXAMPLE 27 |
|---|---|---|---|
| TEGO-BETAINE L-7[10] | 15.0 | 15.0 | 15.0 |
| ADOGEN 141D[3] | 3.0 | — | — |
| ADOGEN 240[4] | — | 3.0 | — |
| ARMEEN DM18D[5] | — | — | 3.0 |
| Deionized water | q.s. | q.s. | q.s. |

| Ingredient | EXAMPLE 28[1] | EXAMPLE 29 | EXAMPLE 30 |
|---|---|---|---|
| MACKAM 1C[11] | 15.0 | 15.0 | 15.0 |
| ADOGEN 141D[3] | 3.0 | — | — |
| ADOGEN 240[4] | — | 3.0 | — |
| ARMEEN DM18D[5] | — | — | 3.0 |
| Deionized water | q.s. | q.s. | q.s. |

[10] Cocamidopropyl betaine, an amphoteric surfactant available as a 35% active material from Goldschmidt Chemical Corporation, Hopewell, VA.; and
[11] Sodium cocoamphoacetate, an amphoteric surfactant, available as a 45% active material from McIntyre Group, Ltd., Chicago, IL.

The compositions of Examples 25–30 were screened for an ability to condition hair by shampooing the hair with a composition, then qualitatively examining the hair for conditioning properties. The compositions of Examples 25–30 each cleaned and conditioned the hair. However, the compositions of Examples 25 and 28, each including a primary amine, outperformed the compositions of Examples 26, 27, 29 and 30 (which include a secondary or a tertiary amine), with respect to conditioning the hair. Accordingly, a shampoo-conditioner composition having a pH of about 6, and including an amphoteric surfactant and a primary amine, effectively cleans and conditions the hair.

The compositions of Examples 1–30 illustrate that a shampoo-conditioner composition including a cleansing surfactant selected from the group consisting of a nonionic surfactant, an amphoteric surfactant and mixtures thereof; a primary amine having about 14 to about 22 carbon atoms; and a sufficient amount of an acid effectively cleans and conditions hair. The presence of an anionic surfactant in the shampoo-conditioning composition severely depresses the ability of the composition to condition the hair. The presence of a quaternary ammonium compound having one long carbon chain containing about 12 to about 18 carbon atoms, a water-soluble amine at pH 6 or a mixture thereof improves the foam generating properties of the composition and does not adversely affect composition performance.

Furthermore, as will be demonstrated in detail hereinafter, the conditioning properties imparted to the hair by a present shampoo-conditioning composition are essentially equal to the conditioning properties imparted to the hair by a composition specifically designed to condition previously shampooed hair. Such a result is unexpected because shampoo-conditioner compositions typically do not condition the hair as well as specifically-designed conditioning compositions. In addition, the present shampoo-conditioner compositions effectively condition the hair without the need for a silicone or hydrocarbon conditioning agent, which are highly effective conditioning agents but are difficult to incorporate into a shampoo-conditioner composition and increase composition instability.

The present shampoo-conditioner compositions effectively clean and condition the hair, and have sufficient esthetic properties for consumer acceptance. Conventionally, shampoo-conditioner compositions include an anionic surfactant to clean the hair and to generate a sufficient foam height for consumer acceptance. The present shampoo-conditioner compositions effectively clean the hair and generate a sufficient foam level in the absence of an anionic surfactant.

In particular, three shampoo-conditioner compositions were prepared. Each composition included 15% by weight of a nonionic surfactant, 3% by weight stearyl amine and a sufficient amount of citric acid to provide a composition pH of 6. The compositions differed only in the identity of the nonionic surfactant. The first shampoo-conditioner composition (including PLANTAREN™ 2000 as the nonionic surfactant) exhibited an initial foam height of 200 ml, whereas the second composition (including TWEEN 20 (polysorbate 20), available from ICI Americas, Inc., Wilmington Del., as the nonionic surfactant) exhibited an initial foam height of 160 ml and the third composition (including TRITON X-100 (octoxynol-9), available from Rohm and Haas, Philadelphia, Pa., as the nonionic surfactant) exhibited an initial foam height of 175 ml. These initial foam heights are sufficient for consumer acceptance. Each of these three compositions also demonstrated an ability to condition hair, and the foam generating ability of each composition was increased by including a quaternary ammonium compound having one long carbon chain of from about 12 to about 22 carbon atoms, such as cetrimonium chloride.

To demonstrate the foam enhancing effects provided by a water-soluble quaternary ammonium compound, the compositions of Examples 31 and 32 were prepared. Initial foam heights were determined by the previously disclosed method.

| Ingredient | EXAMPLE 31[1] | EXAMPLE 32 |
|---|---|---|
| PLANTAREN 2000[6] | 7.5 | 7.5 |
| TEGO-BETAINE L-7[10] | 7.5 | 7.5 |
| BARQUAT CT429[9] | — | 0.3 |
| ADOGEN 141D[3] | 3.0 | 3.0 |
| Deionized water | q.s. | q.s. |
| Foam Height (ml) | 190 | 245 |

The composition of Example 31 exhibited a foam height of 190 ml and effectively cleaned and conditioned hair. The composition of Example 32, further including a water-soluble quaternary ammonium compound, exhibited an increased initial foam height of 245 ml and cleans and conditions the hair as well as the composition of Example 31.

The compositions of Examples 33–36 demonstrate that a water-soluble amine, like a quaternary ammonium compound, increased the foam height generated by the compositions.

| Ingredient | EXAMPLE 33[1] | EXAMPLE 34 | EXAMPLE 35 | EXAMPLE 36 |
|---|---|---|---|---|
| PLANTAREN ™ 2000[6] | 15 | 15 | 15 | 15 |
| ADOGEN 141D[3] | 3 | 3 | 3 | 3 |
| ADOGEN 163D[12] | 1 | — | — | — |
| ARMEEN D18D[5] | — | 1 | — | — |
| BARQUAT CT429[9] | — | — | 1 | — |
| Deionized water | q.s. | q.s. | q.s. | q.s. |
| Foam Height (ml) | 205 | 160 | 195 | 180 |

[12]Lauryl amine, a water-soluble primary amine available from Sherex Chemical Co., Dublin, Ohio.

The compositions of Examples 33–36 each were adjusted to pH about 6. The composition of Example 36 is a control sample that includes neither a quaternary ammonium compound nor a water-soluble amine. The compositions of Example 33 and Example 35, which include a water-soluble amine and a quaternary ammonium compound, respectively, exhibit an increased foam height of 25 ml and 15 ml, respectively. In contrast, the composition of Example 34, which includes a water-insoluble amine, exhibits a foam decrease of 20 ml. Foam heights were initial foam heights, determined by the above-described procedure. The compositions of Examples 33–36 demonstrate the foam enhancing properties of a quaternary ammonium compound and a water-soluble amine having one long carbon chain, and the foam suppression properties of a water-insoluble amine.

To further demonstrate the ability of a present shampoo-conditioner to clean and condition hair, reference is made to the bar graphs of FIGS. 1–6. FIG. 1 illustrates the effect of pH on a shampoo-conditioner composition of the present invention which includes 15% by weight decyl polyglucose (PLANTAREN™ 2000) and 5% by weight stearyl amine. Individual compositions were prepared by the above-described method and adjusted to a pH in the range of about 4 to about 11 with hydrochloric acid. Outside of the pH range of about 4 to about 11, a composition is too acidic or alkaline (i.e., too irritating or corrosive) for contact with the hair or skin. In addition, below a pH of about 4, the hair becomes cationic in nature and is not amenable to conditioning by a primary amine.

The compositions were applied to individual human hair tresses, and the hair tresses were shampooed and rinsed in accordance with standard procedures in the art, for example, panelist combing that utilizes trained judges to rate compositions for an ability to impart conditioning properties to hair shampooed with a composition of the present invention.

In particular, the shampooed hair tresses were judged for combing difficulty by a panel of 13 judges and assessed an average rank of 1 (easiest to comb, i.e., most conditioned) to 6 (most difficult to comb, i.e., least conditioned). For comparison, human hair tresses also were shampooed with either PERT PLUS™, a shampoo-conditioner composition available from Procter and Gamble Co., Cincinnati, Ohio (which is recognized as the benchmark shampoo-conditioner in the industry), or with FINESSE™, a conditioner composition available from Helene Curtis, Inc., Chicago, Ill. (which is recognized as the benchmark conditioner in the industry). Therefore, in this subjective testing, if a composition imparts hair conditioning properties to treated hair equivalent to the properties imparted by FINESSE, the composition is considered an exceptional conditioner because FINESSE is recognized as a benchmark for hair conditioning performance.

In particular, various shampoo-conditioner compositions were tested by applying about one milliliter, or about one gram, of the composition to naturally dark brown tresses of normal virgin human hair, available commercially from DeMeo Brothers, New York, N.Y. The six inch hair tresses, each weighing two grams, were attached to a plastic tab at the root end. In each test, the hair tress was shampooed and the composition was allowed to contact the hair for from 15 seconds to 2 minutes. The hair was rinsed with 32° C. tap water for 30 seconds.

The bar graphs of FIG. 1 illustrate that a premium conditioner composition (FINESSE) typically conditions hair better than a premium shampoo-conditioner composition (PERT PLUS). The bar graphs of FIG. 1 also illustrate that a shampoo-conditioner of the present invention outperforms the benchmark PERT PLUS shampoo-conditioner over the pH range of 4 to 8, and at pH 6 a present shampoo-conditioner composition outperforms the benchmark FINESSE conditioner. Such results are unexpected in the art of shampoo-conditioner compositions.

Samples of the compositions of the present invention used in the preparation of FIG. 1 (i.e., including 15% by weight decyl polyglucose and 5% by weight stearyl amine, adjusted to a pH of 4, 6, 8 or 11) were allowed to dry into a thin dry film. Each dry film was examined by infrared spectroscopy. The infrared spectra were examined at 2000 cm$^{-1}$ and at 1500–1650 cm$^{-1}$ for the amount of amino ($NH_2$) and ammonium ($NH_3^+$) groups present in each composition. Specifically, the infrared spectra revealed that the composition having pH 11 had less than 10% neutralized primary amine (i.e. $NH_3^+$). The composition having pH 8 had greater than 30% and less than 50% neutralized amine. The composition having pH 6 had greater than 50% neutralized amine. The composition having pH 4 had greater than 90% neutralized amine.

Figure 2:
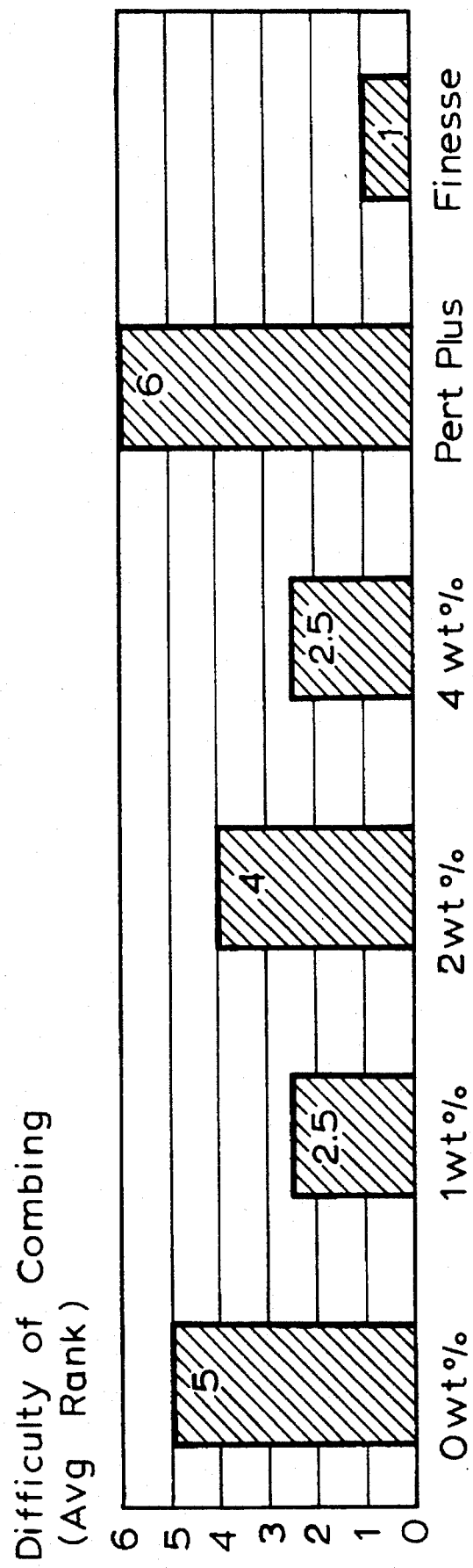
FIG. 2 is a bar graph comparing the combing difficulty of hair shampooed with a composition of the present invention having a variable amount of primary amine and to a commercial shampoo-conditioner (PERT PLUS) and a commercial conditioner (FINESSE)

The bar graphs of FIG. 2 illustrate that increasing the amount of stearyl amine in a shampoo-conditioner composition including 15% decyl polyglucose and at pH 6 generally improves the ability of the composition to condition hair. As shown in FIG. 2, each of the present shampoo-conditioners outperformed PERT PLUS, and a composition including 5% by weight primary amine outperformed FINESSE (FIG. 1).

Figure 3:
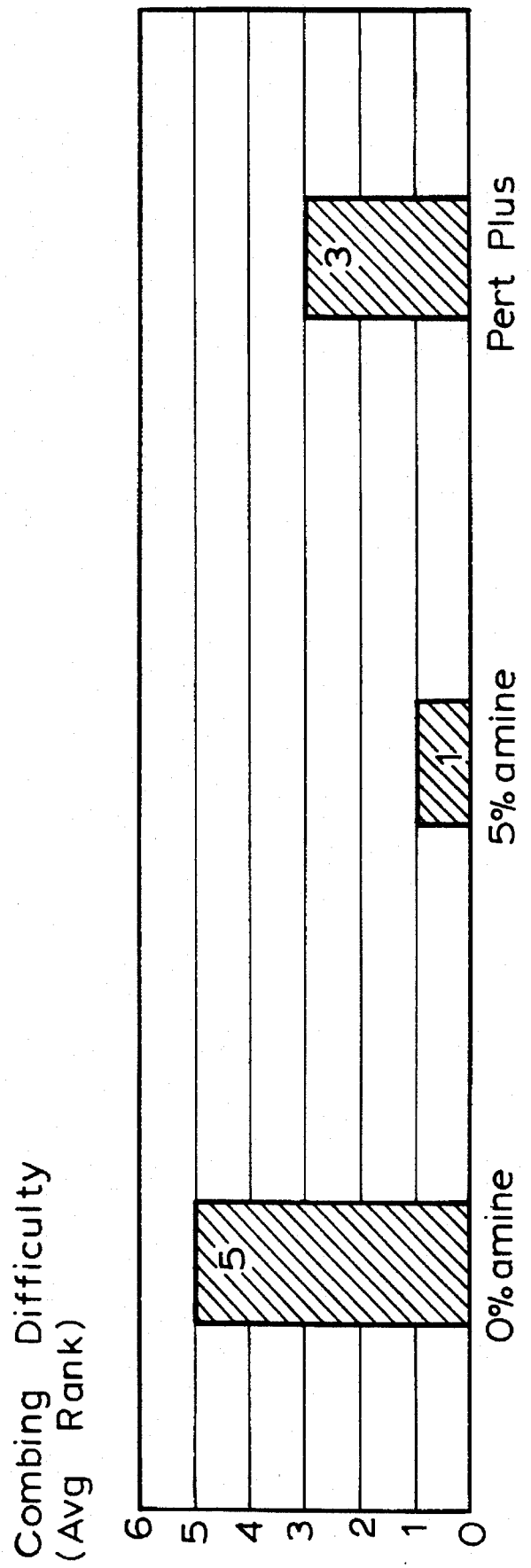
FIGS. 3 and 4 are bar graphs comparing the combing difficulty of hair shampooed with a composition of the present invention to a composition absent a primary amine, to PERT PLUS, and to compositions including an anionic surfactant.
Figure 4:
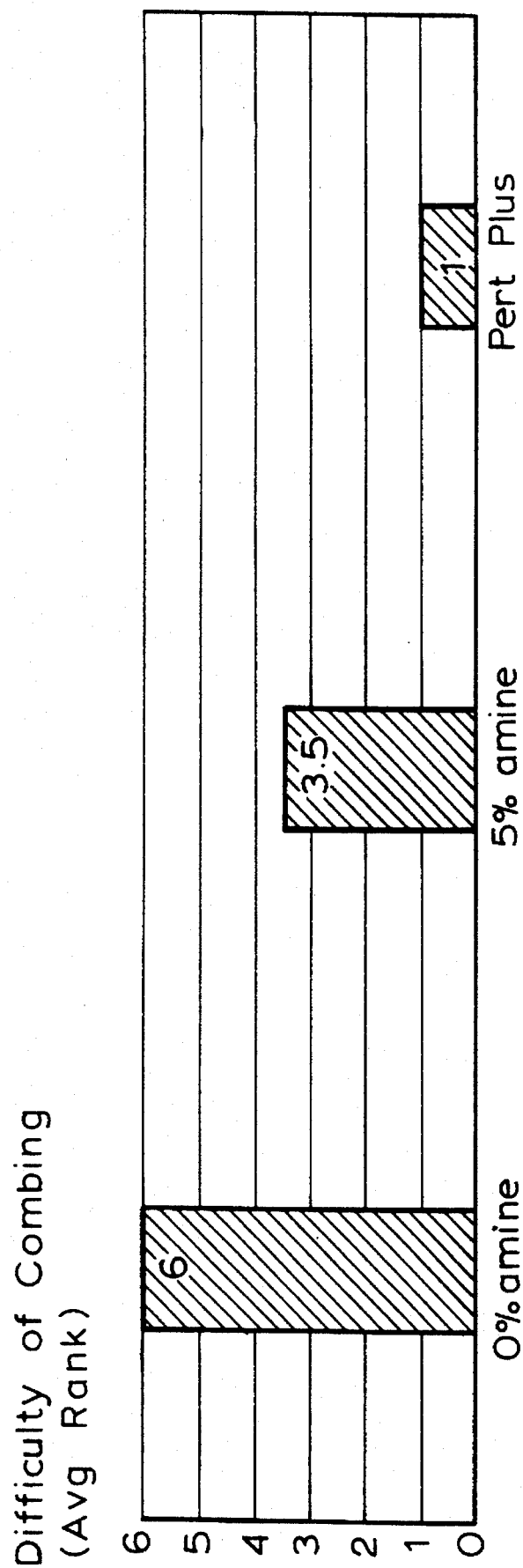

The bar graphs of FIG. 3 illustrate that a present shampoo-conditioner composition including an amphoteric surfactant and 5% by weight primary amine (at pH 6) outperformed PERT PLUS™ with respect to conditioning hair. In comparison, the bar graphs of FIG. 4 illustrate that an anionic-based shampoo-conditioner having pH 6, which further includes stearyl amine, did not condition the hair as well as PERT PLUS™. In summary, the bar graphs of FIGS. 1–4 illustrate that conditioning is maximized at pH about 6, that a nonionic surfactant or amphoteric surfactant is essential with respect to conditioning the hair, that an anionic surfactant is detrimental with respect to hair conditioning, and that a shampoo-conditioner composition of the present invention can condition hair at least as well as FINESSE, the industry benchmark.

Figure 5:
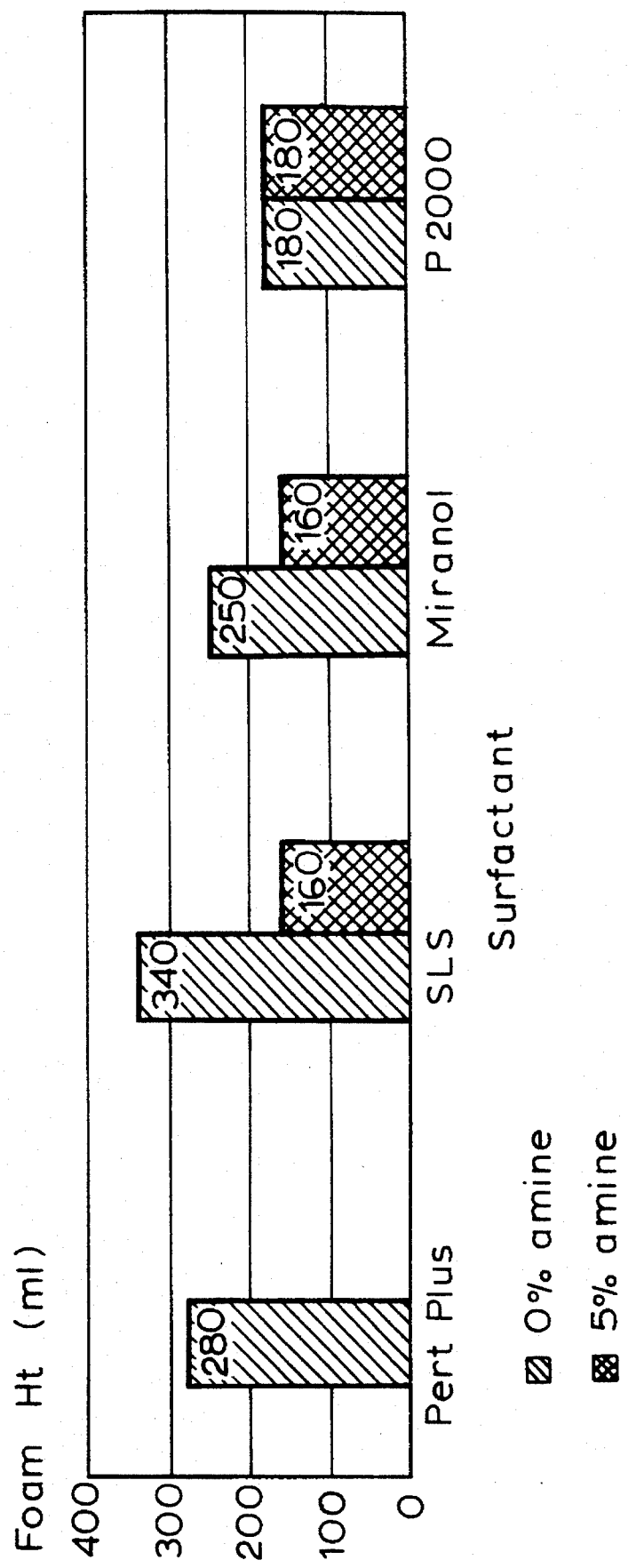
FIG. 5 is a bar graph comparing the foam height of compositions including different classes of surfactants to PERT PLUS.

FIG. 5 illustrates the effect on initial foam height by adding 5% by weight of a primary amine including about 14 to about 22 carbon atoms to a 15% by weight surfactant solution. The initial foam height generated by PERT PLUS™ illustrates a consumer acceptable foam height. The bar graphs of FIG. 5 further illustrate that the foam height of an anionic surfactant (SLS) is decreased more than 50% by adding a primary amine to the composition. The foam height generated by an amphoteric surfactant (MIRANOL C2M) also is decreased, but not as greatly, by adding a primary amine. Surprisingly, the foam height of a nonionic surfactant (PLANTAREN™ 2000) is not adversely affected by adding a primary amine to the composition.

Figure 6:
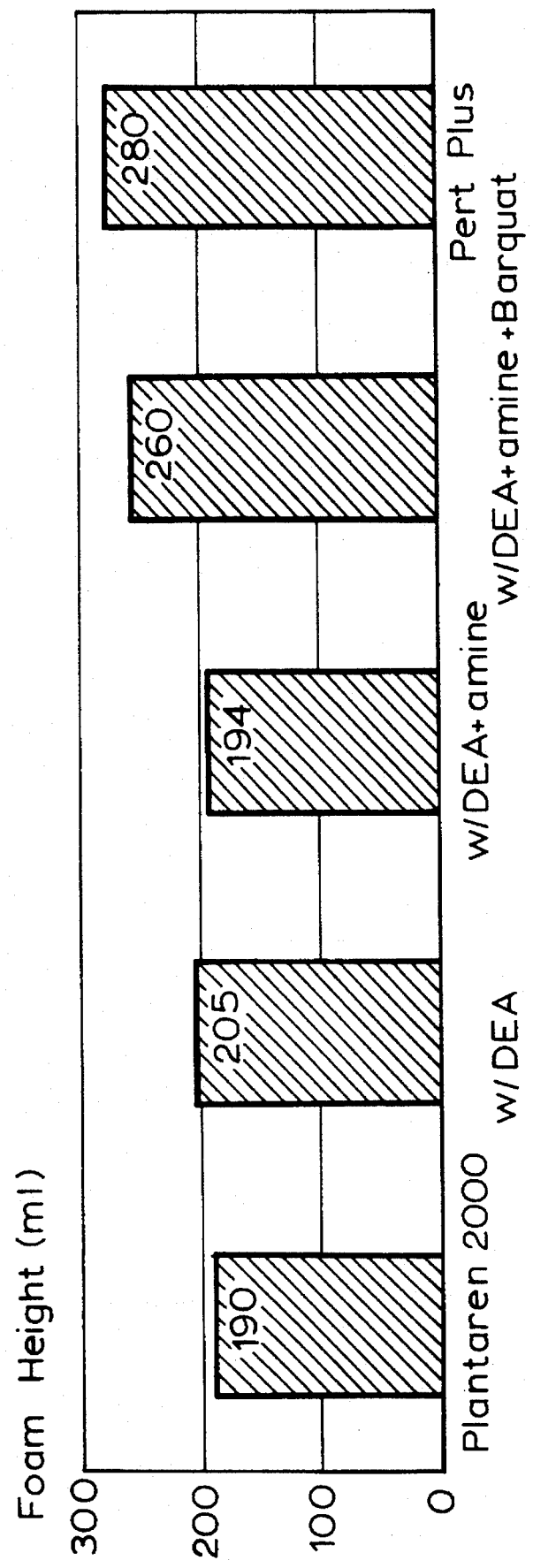
FIG. 6 is a bar graph comparing the foam height of a composition of the present invention to PERT PLUS.

FIG. 6 illustrates that a shampoo-conditioner composition of the present invention can generate an initial foam height almost equal to PERT PLUS™ by incorporating a water-soluble quaternary ammonium compound into the shampoo-conditioner composition. A nonionic alkanolamide (e.g., cocamide DEA) further improves initial foam height. Accordingly, a shampoo-conditioner composition of the present invention can exhibit esthetic products similar to PERT PLUS™, and can condition the hair significantly better than PERT PLUS™ and essentially equal to FINESSE. In addition, a shampoo-conditioner composition of the present invention is mild product having a low irritation potential. For example, a composition including 5% by weight stearyl amine and 15% by weight decyl polyglucose, at pH 6, was classified as having a minimal irritation potential in a standard in-vitro measurement for irritation potential.

Therefore, the method and composition of the present invention provide a shampoo-conditioner composition that exhibits an exceptional ability to simultaneously clean and condition hair. It is both surprising and unexpected for an aqueous composition of the present invention, including a water-insoluble primary amine, to condition hair at least as well as a premium conditioning composition which includes a silicone conditioning agent, like a polydimethylsiloxane, and to effectively clean the hair, while maintaining an acceptable foam level and exhibiting sufficient physical and esthetic properties for consumer acceptance.

Obviously, many modifications and variations of the invention as hereinbefore set forth can be made without departing from the spirit and scope thereof, and therefore only such limitations should be imposed as are indicated by the appended claims.

What is claimed is:

1. A shampoo-conditioner composition comprising:
   (a) about 5% to about 30% by weight of a cleansing surfactant selected from the group consisting of a nonionic surfactant, an amphoteric surfactant and mixtures thereof;
   (b) about 0.5% to about 5% by weight of a primary amine having 14 to 22 carbon atoms;
   (c) a sufficient amount of an acid such that 30 mole percent or more of the primary amine is neutralized, and such that the composition has a pH of about 4 to about 8;
   (d) a carrier comprising water; and
   (e) 0% to about 2% of a water-soluble quaternary ammonium compound having one long carbon chain having 12 to 18 carbon atoms, a water-soluble primary amine having a long carbon chain having 8 to 12 carbon atoms, a water-soluble primary amine having an unsaturated long carbon chain having 8 to 18 carbon atoms, a water-soluble secondary or tertiary amine having a long carbon chain having 8 to 16 carbon atoms, and mixtures thereof, wherein the composition (i) is essentially free of an anionic surfactant and (ii) is free of a silicone conditioning agent and a hydrocarbon conditioning agent.

2. The composition of claim 1 wherein the nonionic surfactant has an HLB value of from about 12 to about 24.

3. The composition of claim 1 wherein the cleansing surfactant is capable of generating an initial composition foam height of 160 milliliters or greater.

4. The composition of claim 2 wherein the nonionic surfactant is selected from the group consisting of an alkanolamide, a block copolymer of ethylene and propylene, an ethoxylated alcohol, an ethoxylated alkylphenol, an alkyl polyglycoside, a polyethylene glycol, a condensation product of ethylene oxide with a long chain amide, an ether of a polyol and a sugar, a laurate ester of ethoxylated sorbitol, and mixtures thereof.

5. The composition of claim 1 wherein the amphoteric surfactant is selected from the group consisting of a betaine, a hydroxypropylsultaine and mixtures thereof.

6. The composition of claim 1 wherein the primary amine is a solid compound at room temperature and has a water solubility of 0.5 grams or less per 100 milliliters of water.

7. The composition of claim 1 wherein the amine is selected from the group consisting of $C_{20-22}$ amine, soya amine, hydrogenated tallow amine, stearyl amine, tallow amine, oleyl amine, hexadecylamine, and combinations thereof.

8. The composition of claim 1 wherein the acid is selected from the group consisting of an inorganic mineral acid, an aliphatic carboxylic acid having up to 5 carbon atoms, and mixtures thereof.

9. The composition of claim 8 wherein the inorganic mineral acid is selected from the group consisting of hydrochloric acid, sulfuric acid, nitric acid, phosphoric acid, and mixtures thereof.

10. The composition of claim 8 wherein the carboxylic acid is selected from the group consisting of acetic acid, lactic acid, citric acid, tartaric acid, propionic acid, butyric acid, pentanoic acid, glycolic acid, and mixtures thereof.

11. The composition of claim 1 having a pH of about 5 to about 7.

12. The composition of claim 1 wherein the cleansing surfactant has an HLB value of about 12 to about 24 and is selected from the group consisting of decyl polyglucose, lauryl polyglucose, cocamide DEA, cocoamphodipropionic acid, sodium cocoamphoacetate cocamidopropyl betaine, polyoxyethylene(20) sorbitan monolaurate, polyoxyethylene(9) octyl phenyl ether, polyoxyethylene(13) lauryl ether, and mixtures thereof; the primary amine is stearyl amine, hydrogenated tallow amine, or a mixture thereof; and the acid is citric acid, hydrochloric acid, or a mixture thereof.

13. The composition of claim 12 further comprising 0.1% to about 1% by weight of cetrimonium chloride, laurtrimonium chloride, lauralkonium chloride, steartrimonium chloride, tallowtrimonium chloride, cetylpyridinium chloride, 2-ethylhexylamine, dodecylamine, dodecyl dimethylamine, hexadecyl dimethylamine, oleyl dimethylamine, cetyl dimethylamine, myristyl dimethylamine, oleyl amine, cocamine, and mixtures thereof.

14. A method of treating hair comprising:
   (a) contacting the hair with a sufficient amount of a shampoo-conditioner composition, said shampoo-conditioner composition comprising:
      (i) about 5% to about 30% by weight of a cleansing surfactant selected from the group consisting of a nonionic surfactant, an amphoteric surfactant and mixtures thereof;
      (ii) about 0.5% to about 5% by weight of a primary amine having 14 to 22 carbon atoms;
      (iii) a sufficient amount of an acid such that 30 mole percent or more of the primary amine is neutralized, and such that the composition has a pH of about 4 to about 8;
      (iv) a carrier comprising water; and
      (v) 0% to about 2% of a water-soluble quaternary ammonium compound having one long carbon chain having 12 to 18 carbon atoms, a water-soluble primary amine having a long carbon chain having 8 to 12 carbon atoms, a water-soluble primary amine having an unsaturated long carbon chain having 8 to 18 carbon atoms, a water-soluble secondary or tertiary amine having a long carbon chain having 8 to 16 carbon atoms, and mixtures thereof,
   wherein the composition (i) is essentially free of an anionic surfactant and (ii) is free of a silicone conditioning agent and a hydrocarbon conditioning agent; and
   (b) rinsing the hair.

15. The method of claim 14 wherein the nonionic surfactant has an HLB value of at least about 12.

16. The method of claim 14 wherein the cleansing surfactant is capable of generating an initial composition foam height of 160 milliliters or greater.

17. The method of claim 15 wherein the nonionic surfactant is selected from the group consisting of an alkanolamide, a block copolymer of ethylene and propylene, an ethoxylated alcohol, an ethoxylated alkylphenol, an alkyl polyglycoside, a polyethylene glycol, a condensation product of ethylene oxide with a long chain amide, an ether of a polyol and a sugar, a laurate ester of ethoxylated sorbitol, and mixtures thereof.

18. The method of claim 14 wherein the amphoteric surfactant is selected from the group consisting of a betaine, a hydroxypropylsultaine and mixtures thereof.

19. The method of claim 14 wherein the primary amine is a solid compound at room temperature and has a water solubility of 0.5 grams or less per 100 milliliters of water.

20. The method of claim 14 wherein the amine is selected from the group consisting of $C_{20-22}$ amine, soya amine, hydrogenated tallow amine, stearyl amine, tallow amine, oleyl amine, hexadecylamine, and combinations thereof.

21. The method of claim 14 wherein the acid is selected from the group consisting of an inorganic mineral acid, an aliphatic carboxylic acid having up to 5 carbon atoms, and mixtures thereof.

22. The method of claim 21 wherein the inorganic mineral acid is selected from the group consisting of hydrochloric acid, sulfuric acid, nitric acid, phosphoric acid, and mixtures thereof.

23. The method of claim 21 wherein the carboxylic acid is selected from the group consisting of acetic acid, lactic acid, citric acid, tartaric acid, propionic acid, butyric acid, pentanoic acid, glycolic acid, and mixtures thereof.

24. The method of claim 14 having a pH of about 5 to about 7.

25. The method of claim 14 wherein the cleansing surfactant has an HLB value of about 9 to about 24 and is selected from the group consisting of decyl polyglucose, lauryl polyglucose, cocamide DEA, cocoamphodipropionic acid, sodium cocoamphoacetate cocamidopropyl betaine, polyoxyethylene (20) sorbitan monolaurate, polyoxyethylene(9) octyl phenyl ether, polyoxyethylene(13) lauryl ether, and mixtures thereof; the primary amine is stearyl amine, hydrogenated tallow amine, or a mixture thereof; and the acid is citric acid, hydrochloric acid, or a mixture thereof.

26. The method of claim 25 further comprising 0.1% to about 2% by weight of cetrimonium chloride, laurtrimonium chloride, lauralkonium chloride, steartrimonium chloride, tallowtrimonium chloride, cetylpyridinium chloride, 2-ethylhexylamine, dodecylamine, dodecyl dimethylamine, hexadecyl dimethylamine, oleyl dimethylamine, cetyl dimethylamine, myristyl dimethylamine, oleyl amine, cocamine and mixtures thereof.

27. A shampoo-conditioner composition comprising:
   (a) about 5% to about 30% by weight of a cleansing surfactant selected from the group consisting of a nonionic surfactant, an amphoteric surfactant and mixtures thereof;
   (b) about 0.5% to about 5% by weight of a primary amine having 14 to 22 carbon atoms;
   (c) a sufficient amount of an acid such that the composition has a pH of about 4 to about 8;
   (d) a carrier comprising water; and
   (e) 0% to about 2% of a water-soluble quaternary ammonium compound having one long carbon chain having 12 to 18 carbon atoms, a water-soluble primary amine having a long carbon chain having 8 to 12 carbon atoms, a water-soluble primary amine having an unsaturated long carbon chain having 8 to 18 carbon atoms, a water-soluble secondary or tertiary amine having a long carbon chain having 8 to 16 carbon atoms, and mixtures thereof,
wherein the composition (i) is essentially free of an anionic surfactant and (ii) is free of a silicone conditioning agent and a hydrocarbon conditioning agent.

* * * * *